United States Patent [19]

Wells

[11] Patent Number: Plant 7,553

[45] Date of Patent: Jun. 11, 1991

[54] DOUGLAS-FIR TREE "TORQUIS" VARIETY

[75] Inventor: Stephen P. Wells, Moscow, Id.

[73] Assignee: The United States of America as represented by the Secretary of Agriculture, Washington, D.C.

[21] Appl. No.: 341,088

[22] Filed: Apr. 20, 1989

[51] Int. Cl.[5] ..... A01H 5/00

[52] U.S. Cl. ..... Plt./50

[58] Field of Search ..... Plt./50

[56] References Cited

U.S. PATENT DOCUMENTS

P.P. 5,457 4/1985 Holden ..... Plt. 50

P.P. 5,711 4/1986 Sturrock ..... Plt. 50

OTHER PUBLICATIONS

P. Den Ouden et al., 1985, "Manual of Cultivated Conifers—Hardy in the Cold- and Warm-Temperate Zone", The Hague, printed in the Netherlands, pp. 368–377.

*Primary Examiner*—Howard J. Locker

*Attorney, Agent, or Firm*—M. Howard Silverstein; John D. Fado; William J. Connors

[57] ABSTRACT

A new and distinct variety of Douglas-fir, *Pseudotsuga menziesii*, variety "Torquis", an intervarietal hybrid of coastal variety (*Pseudotsuga menziesii* var. menziesii) and inland variety (*Pseudotsuga menziesii* var. glauca), having generally upright growth with a curving, twisting, non-directional, at times corkscrew-like pattern to stem and branches, and smaller than average size, while retaining the foliage color and foliage character of a normal Douglas-fir, was discovered in a Douglas-fir test planting on a site near Grangeville, Id., and was asexually reproduced by rooting and grafting.

3 Drawing Sheets

1

This invention relates to a new and distinct variety of Douglas-fir (*Pseudotsuga menziesii*), referred to as the variety "Torquis".

The "Torquis" variety was discovered growing in a Douglas-fir test planting established by the Genetics and Pest Resistance Work Unit of the Intermountain Research Station, Forest Service, U.S. Department of Agriculture, Moscow, Id. The test planting was established in 1975 and 1976 on a site near Grangeville, Id., at Latitude 45°58′ Longitude 115°53′, on U.S. Forest Service land managed by the Nez Perce National Forest.

The test planting was established to assess the performance of Douglas-fir intervarietal hybrids and includes coastal variety (*Pseudotsuga menziesii* var. menziesii), inland variety (*Pseudotsuga menziesii* var. glauca), and hybrids developed from control-pollinated crosses on inland variety trees using pollen from coastal variety trees.

During an evaluation of survival and field performance in 1984, one of the hybrid families was found to include several individuals of a different growth habit. One tree, the "Torquis" mother tree, was outstanding and quite unique in growth habit, foliage color and size.

The primary features of the new and distinct "Torquis" variety that distinguish it from related known varieties are:

1. a growth habit in which the tree grows generally upright with branches regularly borne and normal in length, but with the stem and all branches having a curving, twisting, non-directional, at times corkscrew-like pattern, the stem and branches having this pattern from beginning of elongation to maturity;

2. an 8½ foot height at age 17 that is small compared to the 14 to 15 foot average height of a normal Douglas-fir tree of the same age; and, 3. foliage color and character that remains the same as that of the foliage of a normal Douglas-fir.

2

The "Torquis" variety expresses the twisting growth habit and smaller size while retaining the foliage color, foliage character and vigor of a normal, healthy Douglas-fir tree.

The "Torquis" mother tree was asexually reproduced by rooting branch cuttings in 1984. Additional reproduction was done in 1985 and 1986 by grafting and in 1987 by rooting cuttings.

All asexual reproduction was done in Moscow, Id., and all such asexual reproduction has resulted in individuals possessing the same characteristics as the Torquis mother tree. Rooted cuttings retain the same growth habit, color and vigor, and subsequent grafts of material taken from the rooted cuttings also retain the same growth habit, color and vigor.

Figure 1:
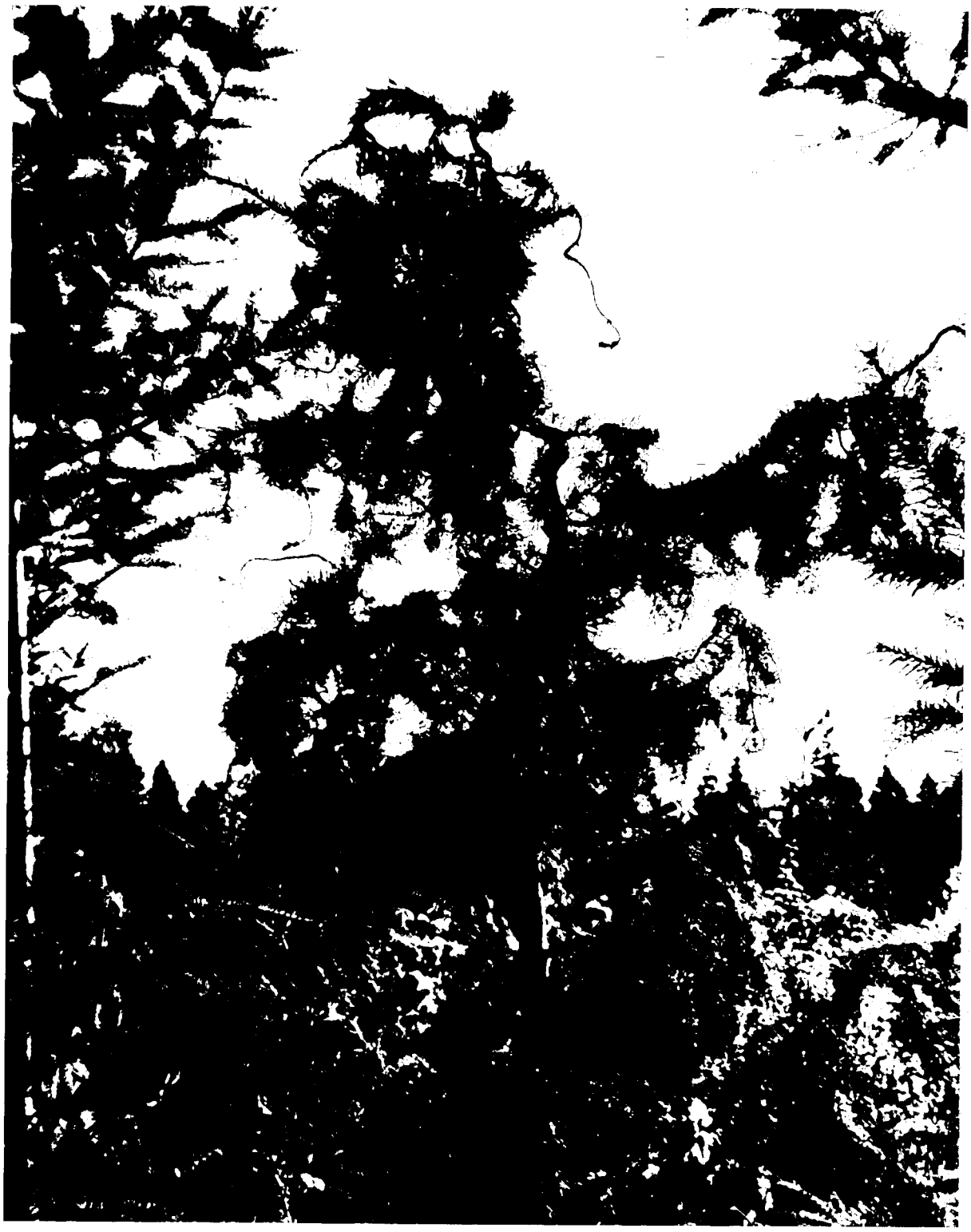
FIG. 1 illustrates the "Torquis" mother tree with its unique growth habit. The mother tree is shown at age 17 with its height at about 8½ feet.
Figure 2:
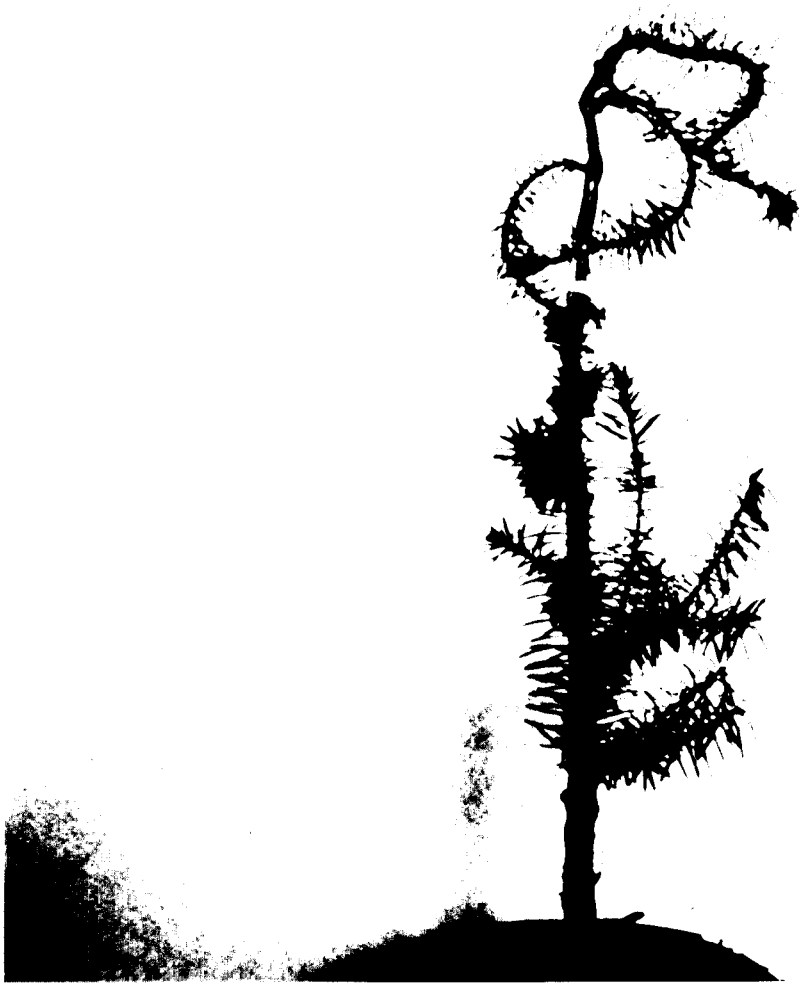
FIG. 2 is a graft of "Torquis" onto a normal Douglas-fir seedling, showing the normal growth habit of the lower root stock branches compared to the Torquis top.
Figure 3:
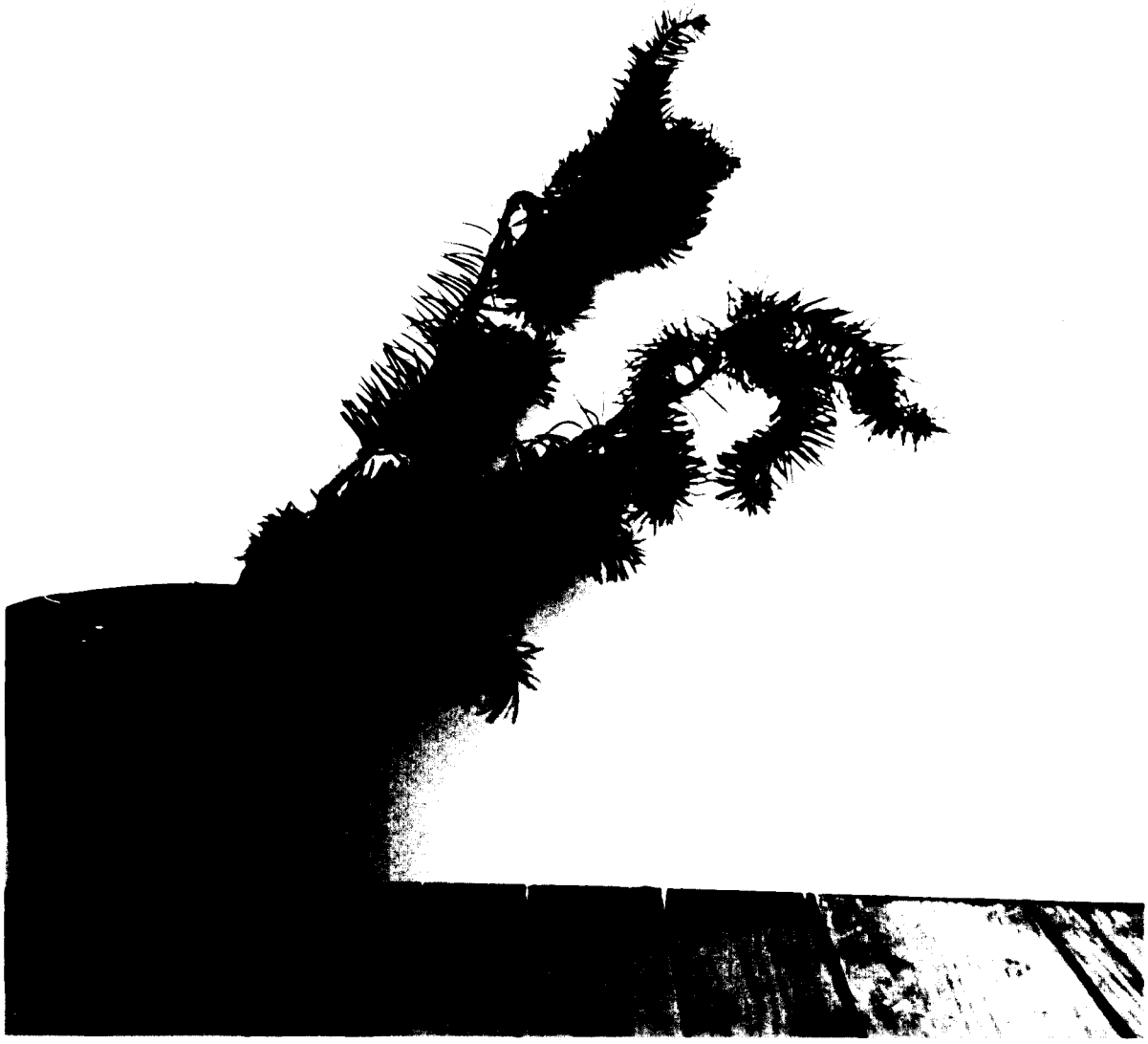
FIG. 3 is a 1988 photograph of a rooted cutting that was rooted in 1984.

The following is a detailed description of the new and distinct variety, with color comparisons based on the Munsell color system for plant tissues:

Parentage: Inland Douglas-fir (*Pseudotsuga menziesii* var. glauca)×Coastal Douglas-fir (*Pseudotsuga menziesii* var. menziesii); the individual parents were not identified.

Type: Evergreen Conifer.

Location where mother tree grown: Nez Perce National Forest, near Grangeville, Id., Latitude 45°58′, Longitude 115°53′.

Size: Mother tree is about 8½ feet tall at age 17, which is about 60% of the average height of a normal Douglas-fir tree of the same age; two four-year-old rooted cuttings are about 18 inches tall.

Growth habit: Generally upright, with branches regularly borne and normal in length, but with the stem and all branches having a curving, twisting, non-directional, at times corkscrew-like pattern from the beginning of elongation to maturity.

Growth rate: Grafts on three-year-old rootstocks have been averaging about eight inches of new growth per year for two years.

Bark characteristics and color: The color of mature bark is 2.5 GY 6/2, and the color of young bark (in June) is 2.5 GY 6/10.

Dormant bud color: 2.5 YR 4/4 to 4/8.

Bud characteristics: Same as a normal Douglas-fir.

Fruits: None observed.

Foliage characteristics: Needle-shaped, evergreen, rigid, from 2½ to 4½ cm long.

Foliage color: Dark green, like foliage of a normal Douglas-fir, the color of the needles being 5 GY 3/4 when mature and 5 GY 6/4 when young (in June).

Cones: None observed.

Seeds: None observed.

Propagation: Asexual reproduction by rooting and grafting of branch tips.

I claim:

1. A new and distinct variety of Douglas-fir, *Pseudotsuga menziesii,* substantially as shown herein and described, characterized particularly by generally upright growth with a curving, twisting, non-directional, at times corkscrew-like pattern to stem and branches, and smaller than average size, while retaining the foliage color and foliage character of a normal Douglas-fir.

* * * * *